United States Patent [19]
Taylor et al.

[11] Patent Number: 5,776,154
[45] Date of Patent: Jul. 7, 1998

[54] SURGICAL INSTRUMENTS FOR MAKING PRECISE INCISIONS IN A CARDIAC VESSEL

[75] Inventors: Charles S. Taylor, San Francisco; John J. Frantzen, Copperopolis; Ivan Sepetka, Los Altos, all of Calif.

[73] Assignee: Cardiothoracic Systems, Inc., Cupertino, Calif.

[21] Appl. No.: 603,329

[22] Filed: Feb. 20, 1996

[51] Int. Cl.$^6$ ............................................. A61B 17/32
[52] U.S. Cl. ................................. 606/167; 606/170
[58] Field of Search ........................... 606/167, 166, 606/170, 174, 148, 113

[56] References Cited

U.S. PATENT DOCUMENTS

| | | | |
|---|---|---|---|
| 5,304,190 | 4/1994 | Reckelhoff et al. | 606/170 |
| 5,314,440 | 5/1994 | Shapiro | 606/167 |
| 5,397,333 | 3/1995 | Knoepfler | 606/167 |
| 5,562,693 | 10/1996 | Devlin et al. | 606/166 |

OTHER PUBLICATIONS

"Direct Myocardial Revascularization by Saphenous Vein Graft," R.G. Favaloro, M.D.; D.B. Effler, M.D.; L.K. Groves, M.D.; W.G. Sheldon, M.D.; and F.M. Sones, Jr., M.D. *The Annals of Thoracic Surgery*, vol. 10, No. 2, Aug., 1970.

Geister product insert for Article No. 16–1020, Diamond Knife for Coronary Surgery.

*Primary Examiner*—Michael Buiz
*Assistant Examiner*—Kevin Truong
*Attorney, Agent, or Firm*—Lyon & Lyon LLP

[57] ABSTRACT

Surgical instruments and methods for making substantially linear incisions, especially through the wall of vessels, such as arteries, specifically designed for coronary artery bypass graft procedures (CABG) on the beating heart. The invention is particularly useful to create the incision in the artery to which a bypass graft is sewn, typically the left anterior descending artery (LAD). The instruments allow incisions to be rapidly made, precisely measured, and cleanly formed so that a bypass graft can be rapidly sewn in place, without undue trauma to surrounding tissue and excessive loss of blood. In one embodiment, a hand-held instrument has a cutting edge formed on the interior edge of a curved blade fixed near the end of the instrument. The tip of the blade has a point for penetrating the vessel wall which may have several alternate shapes to facilitate penetration of the vessel wall while minimizing trauma to the surrounding tissue. In another embodiment the hand-held instrument includes a moveable member which creates an incision by engaging a cutting blade against a stop, cutting tissue therebetween, the stop including a pointed tip similar to the previous embodiment. In another embodiment, the instrument features a motion-canceling member which compensates for the movement of the target surface to be incised. This embodiment has a cutting blade which is manipulated from a handle which is isolated from the movement of the tissue containing or proximate to the target of the incision.

2 Claims, 4 Drawing Sheets

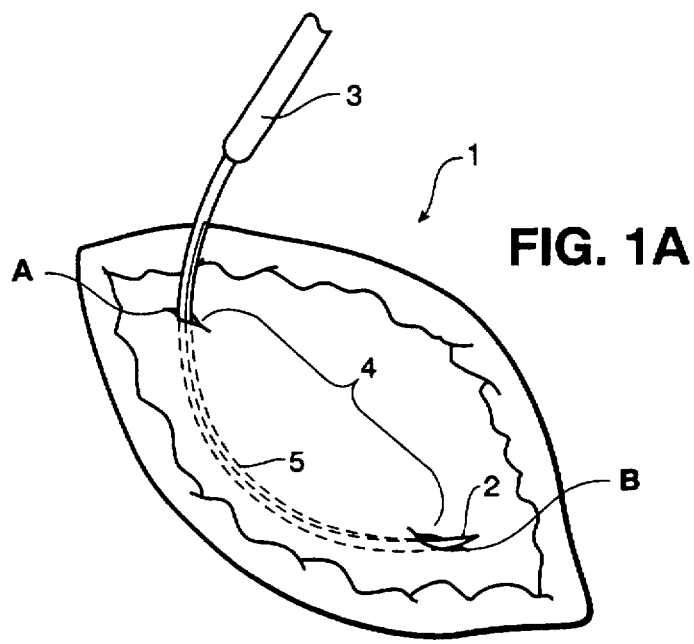
FIG. 1A
FIG. 1B
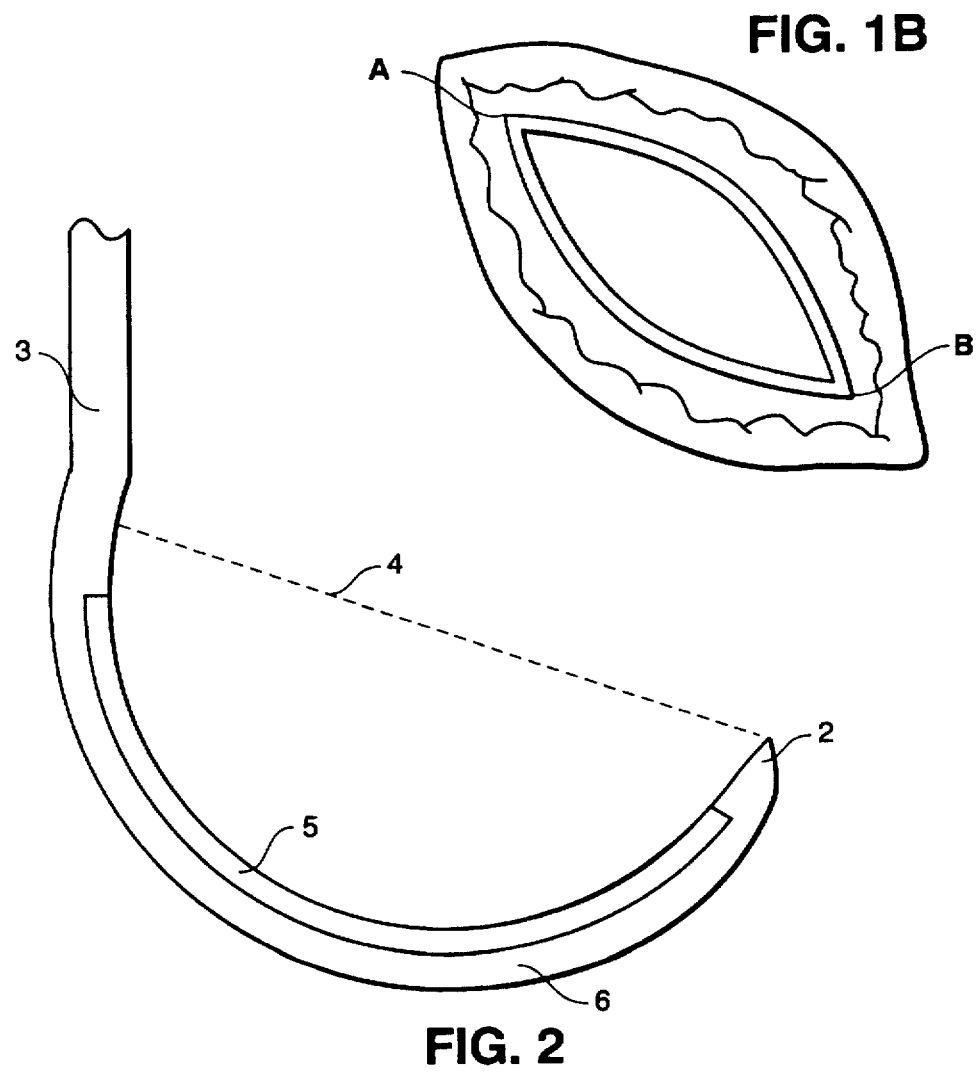
FIG. 2

SURGICAL INSTRUMENTS FOR MAKING PRECISE INCISIONS IN A CARDIAC VESSEL

The most common technique for coronary artery bypass graft (CABG) surgery requires arresting the heart and attaching a patent to a cardiopulmonary bypass machine to preserve the flow of oxygenated blood during the procedure. This technique also requires splitting the sternum, followed by placing large bore cannulas in the arterial and venous sides of the heart to circulate blood through an extracorporeal pump. The heart is chilled to reduce the myocardial oxygen demand and the bypass graft is installed on a non-beating heart. The common technique is lengthy and traumatic to the patient and carries all of the attendant risks of cardiopulmonary bypass.

In recent years, surgeons have begun performing CABG surgery on the beating heart, without the use of extracorporeal circulation. The beating heart CABG procedure uses smaller incisions, avoids the use of the extracorporeal pumps, and permits the graft procedure to be accomplished without splitting the sternum. When the beating heart CABG procedure is employed, a number of advantages are observed: patients who are treated without extracorporeal circulation recuperate faster, the hospital stay is shorter and less costly, the need for a postoperative mechanical ventilator is reduced, and the amount and frequency of blood transfusions is also reduced.

Despite the advantages, the beating-heart CABG procedure is not widely practiced, in part, because of the difficulty in performing the necessary surgical procedures while the heart is still beating using conventional instruments. If special designed instruments were available to assist the surgeon in performing the CABG procedure on the beating heart, the procedure would be more widely practiced and the treatment of a significant patient population would be improved.

These instruments must be specially designed to facilitate less invasive procedures where minimally sized incisions are placed in the chest. In many surgical procedures, such as the beating-heart CABG procedure, the instrument must be manipulated through a comparatively small opening in the chest and at a distance of at least several inches from the tissue being incised. Thus, instruments must be specially designed to enable the surgeon to complete all the phases of the surgery by remote manipulation through small openings in the chest cavity. Additionally, because the heart may remain beating throughout the operation, the procedures must be performed quickly, and without undue trauma to the tissue, and must not cause excess loss of blood.

In many surgical procedures, including the beating-heart CABG procedure, the surgeon must make a substantially linear incision in a vessel, such as an artery which carries blood to the heart. The incision must completely penetrate a portion of one side of the wall of the vessel to create an opening without damaging the surrounding tissue, including in particular, the interior walls of the vessel proximate to the site of the incision. In the CABG procedure, it is particularly important for the surgeon to create a straight, uniform incision through a portion of the vessel wall because a precise incision through the wall of a vessel is necessary to create the opening to which an anastomosis will be sewn and through which blood ultimately will flow. In such cases, the surgeon creates an incision in a vessel to receive the anastomosis, which is completed when the connection is sewn to the periphery of the opening in the artery to re-establish blood flow.

Currently, many surgeons begin making the incision in the artery with a scalpel or with the point of a pair of surgical scissors and then manually cut the incision to the desired length by a series of scissor cuts or by manually passing the scalpel through the wall of the vessel for the entire length of the incision. These current techniques have several disadvantages which are particularly problematic in a beating-heart procedure. In cardiac surgery on the beating heart, the surgical field is small, and it is difficult for the surgeon to precisely manipulate the instruments. The surgeon must make a clean incision completely through one wall of a small vessel without damaging the interior surface of the vessel opposite the location of the incision or the surrounding tissue. The current techniques are also time consuming, imprecise in creating an incision of an exact length, and may cause undue trauma to the surrounding tissue, especially when the tissue is moving due to the motion of the heart. Because blood flow through the vessel may be interrupted during the beating heart CABG procedure, it is also important that the entire incision be made rapidly. If the current techniques result in an incision which is poorly formed, this may lengthen the procedure and adversely affecting the patency of the graft when it is sewn to the periphery of the incision.

SUMMARY OF INVENTION

This invention is surgical instruments which facilitate precise and substantially linear incisions, especially through the wall of vessels, such as arteries, and which have been specially designed for coronary artery bypass graft procedures (CABG) on the beating heart. The instruments of this invention are particularly useful to create the incision in the target artery to complete an anastomosis, typically the left anterior descending artery (LAD), although the actual site for any particular patient is determined clinically. The instruments of the invention allow incisions to be rapidly made, precisely measured, and cleanly formed so that the bypass graft can be rapidly sewn in place. The instruments of the invention also result in less trauma to the vessel and require fewer manipulations of the vessel by the surgeon. This can be particularly significant where the interior of the vessel contains lesions or deposits. Although features of the instruments of the invention have particular utility for beating-heart CABG procedures, the instruments described here can be advantageously used in other procedures where similar conditions to the beating-heart CABG procedure exist.

In one embodiment, the invention is a hand-held instrument with a curved cutting edge formed on the interior edge of a curved or arcuitous segment located near the end of the instrument. The tip of the instrument has a point for penetrating the vessel wall. The point may have several alternate shapes to facilitate penetration of the vessel wall while minimizing the trauma to the surrounding tissue. Alternatively, the cutting surface maybe disposed on one or more straight surfaces at the terminal end of the instrument.

Another embodiment is comprised of a hand-held instrument with a movable shaft member such that the incision is created by engaging a cutting edge against a blade stop with the tissue being cut therebetween. This instrument is also constructed to facilitate rapid linear incisions in a vessel while minimizing the possibility for damage to the surrounding tissue.

In another embodiment, the instrument features a motion-cancelling member which compensates for the movement of the target surface to be incised. This embodiment has a cutting blade which is manipulated from a handle which is isolated from the movement of the tissue containing or proximate to the target of the incision.

DESCRIPTION OF THE FIGURES

FIGS. 1A and 1B illustrate an embodiment of the invention used to create an incision in a vessel along line segment AB.

FIG. 2 is a detailed view of the portion of the instrument of one embodiment of the invention showing the cutting edge.

DETAILED DESCRIPTION OF THE INVENTION

Figure 3:
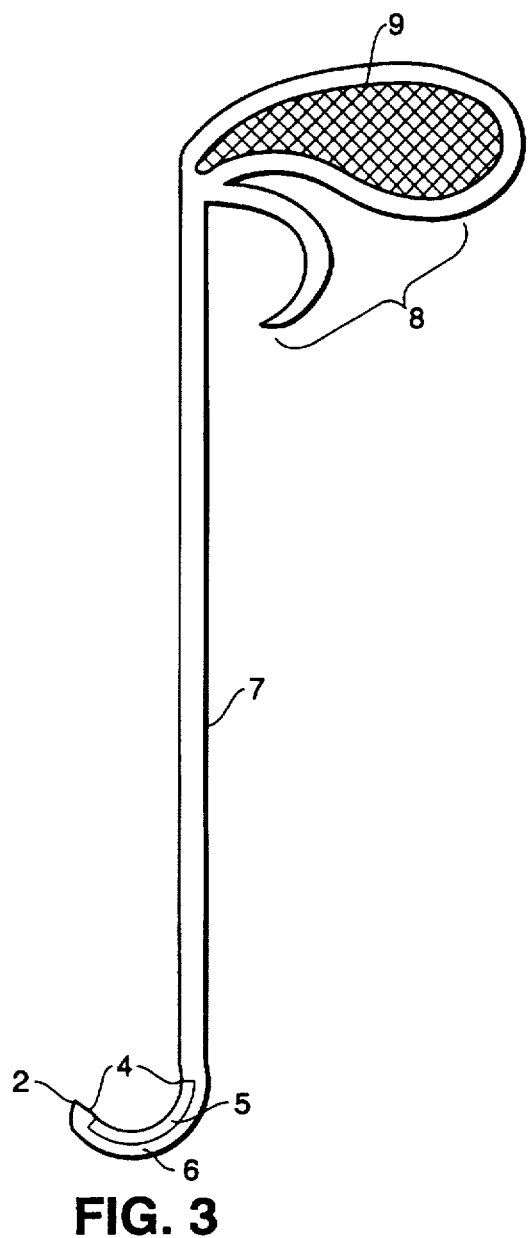
FIG. 3 illustrates a side view of one embodiment of the invention.

Referring to FIG. 1, the procedure whereby the surgeon makes an incision in a vessel 1 at the point at which a graft will be sewn about the periphery of the incision may be illustrated using an embodiment of the invention to make an incision between points A and B. When the vessel is an artery, in particular, a coronary artery, this procedure is known as an "arteriotomy". Before beginning the incision, the surgeon determines an appropriate site to make the incision in the vessel 1. The site of the appropriate incision is the site which the surgeon has identified as the location on the vessel at which the anastomosis will be completed. The incision is generally linear and penetrates the entirety of one wall of the vessel such that the incision spans a line segment between two points A and B as shown in FIGS. 1A and 1B. To make the incision using an embodiment of the instrument of the invention, the surgeon inserts the point 2 of the instrument 3 through point A, completely penetrating the outer wall of the vessel 1. The surgeon may then orient the instrument 3, without making a further incision in the vessel 1, by inserting the portion of the instrument 3 containing the cutting edge 5 into the vessel 1 such that the point 2 of the instrument 3 is proximate to point B and such that the portion of the instrument 3 inside the vessel is comprised of the portion of the instrument 3 which features the cutting edge 5 At this point, for one embodiment of the invention, a curved portion 4 of the instrument 3 comprising the cutting edge 5 is inside the vessel and the surgeon can visualize the location of the desired end point of the incision B on the vessel 1. The blunt portion of the instrument is located on the curved portion 4 opposite the cutting edge 5 to avoid damage to the vessel 1 opposite the incision. To determine the location of the point 2 of the instrument 3 relative to point B, the surgeon may orient the instrument 3 such that the point 2 pushes lightly on the inside of the vessel 1 such that the location of the point 2 can be observed visually. When the point 2 of the instrument coincides with point B, the surgeon manipulates the instrument 3 to push the point 2 through the vessel 1 from the inside such that the point 2 of the instrument 3 protrudes through point B.

At this stage, as illustrated in FIG. 1A, a linear incision has not yet been made, the portion of the instrument 3 containing the cutting edge 5 has penetrated the vessel 1 at points A and B, and in one embodiment, the curved portion 4 of the instrument 3, which features the cutting edge 5, is inside the vessel 1. By drawing the instrument 3 away from the vessel 1, while keeping the cutting edge 5 of the instrument 3 in a plane which contains line segment AB, the surgeon, in a single action, creates a clean, precisely measured and substantially linear incision in the vessel 1 from point A to point B as illustrated in FIG. 1B. This incision is well formed for receiving a graft which will be sewn about the periphery of the incision thus created. By following the above technique, an ideal incision for receiving a graft can be made in a few seconds with minimal chance of damage to the surrounding tissue or the interior surface of the vessel 1. An additional advantage is that the loss of blood from inside the vessel 1 is minimized until the time at which the surgeon is prepared to make the entire incision.

Referring to FIG. 2, the curved portion 4 of the instrument of one embodiment of the invention is generally arcuitous and may comprise a portion of a circle, and is most preferably less than a semi-circle. The cutting edge 5 is contained within the curved portion 4 of the instrument and may comprise the entire curved portion 4. The curved portion 4 of the instrument terminates in a point 2 which is shaped to penetrate the vessel wall.

In an alternate embodiment, the cutting edge 5 is placed on a straight member (not shown) which extends from the distal (lower) end of the instrument. The extension contains the cutting edge which may also comprise a portion of the shaft of the instrument 3.

Referring to FIG. 2, the curved portion 4 has a cutting edge 5 on the upper surface of the curved portion 4 of the instrument 3. The width of the curved portion 4 may be approximately 0.070, but may very depending on the application, and should not be substantially thicker than the vessel to be incised. The embodiment shown in FIG. 2 is manufactured from an oval-shaped blank, although the shape is not critical. The cutting surface may be created by any of several techniques well known to those of ordinary skill such as milling, EDM, etc. The material preferred for the cutting surface is stainless steel. The body of the instrument 3 may be plastic having the stainless steel cutting surface attached thereto. In the example of FIG. 2, the cutting edge 5 is preferably created in the portion of the instrument 3 comprising the majority of the length of the curved portion 4 of the instrument. The opposing surface 6 of the curved portion 4 of the instrument 3 is preferably smooth and rounded to avoid damaging the interior walls of the vessel 1 when inserted therein.

Referring to FIG. 3, the curved portion 4 and cutting edge 5 form a distal (lower) portion of a hand-held embodiment of the invention having a shaft 7 and a handle 8 with a grip portion 9 to facilitate the instrument 3 being manipulated by hand.

Figure 4A:
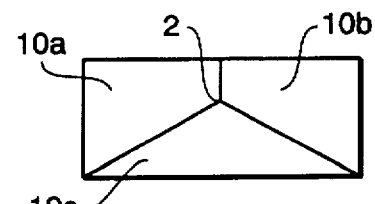
FIGS. 4a–4e illustrates alternate designs for the structure of the point used with certain embodiments of the invention.
Figure 4B:
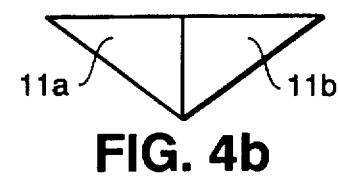
Figure 4C:
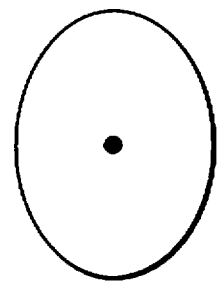
Figure 4D:
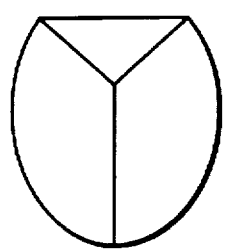
Figure 4E:
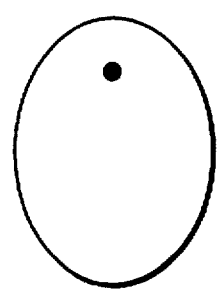

Referring to FIGS. 4a–4e, the point 2 of the instrument may have several alternative designs and shapes depending, in part, on the structural characteristics of the vessel to be incised. The point 2 of FIG. 4a and 4d has three facing surfaces 10a, 10b and 10c which form the point 2 at the point of their convergence. Similarly, in FIG. 4b, a point is formed at the convergence of two facing surfaces 11a, 11b which form a point at the convergence with the surface of the curved portion 4 of the instrument 3. Referring to FIGS. 4c and 4e, the point may be formed from a cylindrical portion of the tool which has a continuously decreasing diameter to form a pin-like point 2, which may be offset of center (FIG. 4e).

Figure 5:
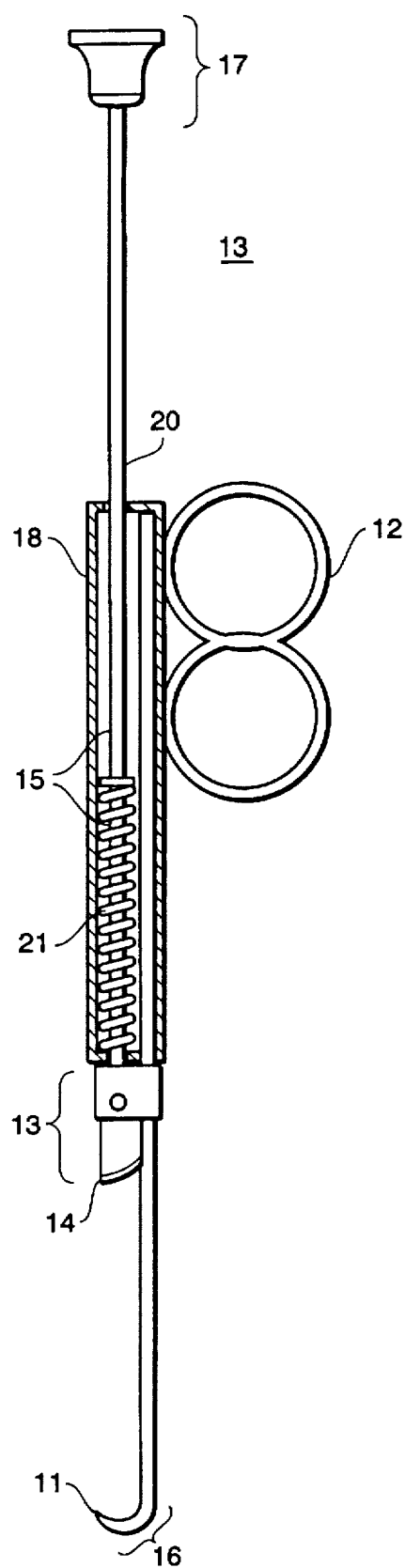
FIG. 5 is an embodiment of the invention which has a movable shaft member, a cutting edge, and a blade stop to achieve the incision.

Referring to FIG. 5, in another embodiment, a cutting edge 14 is mounted on a blade member 13 attached to a movable shaft member 15 which comprises a rigid shaft 20 and moves vertically along the length of the instrument 13 and operably engages a blade stop 16 which defines the range of motion of the movable shaft member 15 and terminates the downward movement thereof. The cutting edge 14 and the blade stop 16 are operably engaged when each contacts the other to cut tissue positioned therebetween. In the beating heart CABG procedure, the blade stop 16 is manipulated in a manner similar to the embodiment described above and in FIG. 2 and as shown in FIG. 1. However, in this instance, the blade stop 16 is inserted into the vessel and oriented such that the cutting edge 14 and the blade stop 16 are brought together to create an incision at the desired location in the artery wall.

The downward motion of movable shaft member 15 of the instrument is controlled by a thumb control 17 attached to the a shaft 20. Thus, the movable shaft member 15 and cutting edge 14 are actuated from a thumb control at the proximal (upper) end of the instrument proximate to the grip of the instrument. The rigid shaft 20 passes into and is contained within the housing 18 of the instrument. In a preferred embodiment, the movable shaft member 15 is tensioned with a pressure spring 21 such that the moveable shaft member 15 remains retracted and the cutting edge 14 and the blade stop 16 are restrained from engaging in another until the blade stop 16 is positioned in the vessel and until the incision is desired to be made. The housing 18 of the instrument of this embodiment of the invention may have several structural and design alternatives and modifications without altering the essential function of the device. In essence, the housing 18 of the instrument provides a hand-held structural portion which is fixed relative to the movable shaft member 15 such that the movable shaft member 15 can move vertically to engage the cutting edge 14 and blade stop 16 to readily accomplish the incision. The housing 18 of the instrument may be hollow, containing the movable shaft member 15, the rigid shaft 20 and guide means, such as a rail, which enables reproducible linear movement of the movable shaft member 15.

Figure 6A:
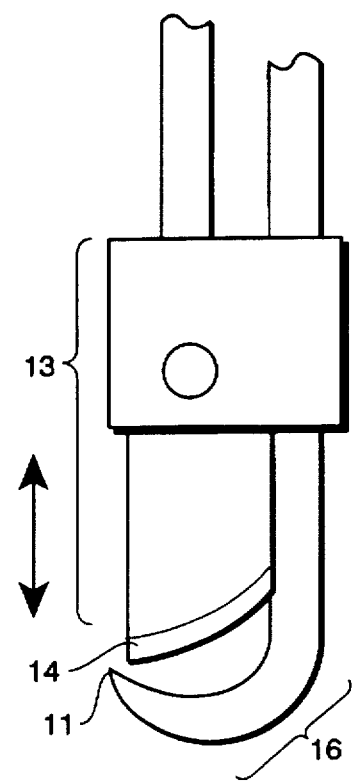
FIGS. 6a and 6b illustrate an embodiment of the invention wherein the movable shaft member with the cutting edge engages the blade stop of FIG. 5 together with the cutting edge with which it becomes operably engaged.
Figure 6B:
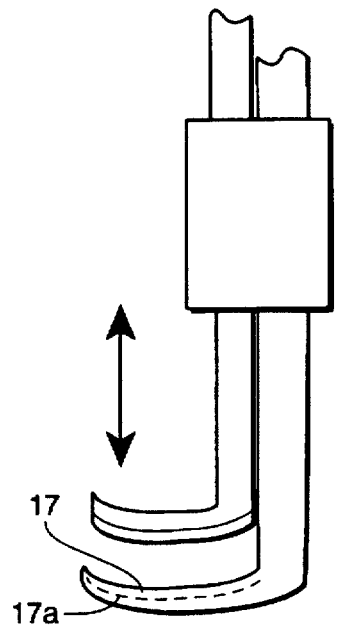

Referring to FIG. 6, the blade stop 16 is designed to penetrate the vessel with a point 11 substantially as described in connection with the embodiment of FIGS. 1–3. The point may have any of the shapes or configurations depicted in FIGS. 4A–4E incorporated into the blade stop 16. The structure of the blade stop 16 proximate to the point 11 is shaped to function as the blade stop 16 for the cutting edge 14 by having a complementary shape such that when the cutting edge 14 operably engages the blade stop 16, the tissue or other structure therebetween is cut. Preferably, the blade stop 16, has an upper surface 17 at the terminal end of the instrument having a groove 17a or like structure disposed in the upper surface 17 such that the cutting edge 14 fits conformingly therein. The overall length of the blade stop 16 also may be varied to accommodate the desired length of the incision or may match the length and configuration of the cutting edge 14. Depending on the application, the cutting edge 14 and blade stop 16 may have sufficient length to perform the desired incision in one cycle of the instrument. Alternatively, several cycles of the instrument may be performed. As in the first embodiment described above, the bottom surface of the portion of the tool inserted into the artery the is smooth to avoid damage to the interior portion of the vessel opposite the site of the incision. The housing 18 may also be a substantially closed cylindrical structure with the movable shaft member is contained entirely within. The direction of movement of the movable shaft member 15 is preferably controlled by a series of guides which surround the movable member 15 in an annular fashion to provide controlled linear movement when the cutting edge 14 engages the blade stop 16 to achieve the desired incision. The instrument may also have a gripping means such as finger rings 12 or other such structures to facilitate being held by hand. The movable shaft member 15 may be spring-loaded such as by a spring 21 coiled between the thumb control 17 and the housing 18 of the instrument or may be otherwise tensioned by conventional means in either direction such that the cutting edge 14 and blade stop 16 are drawn together or apart.

Figure 7:
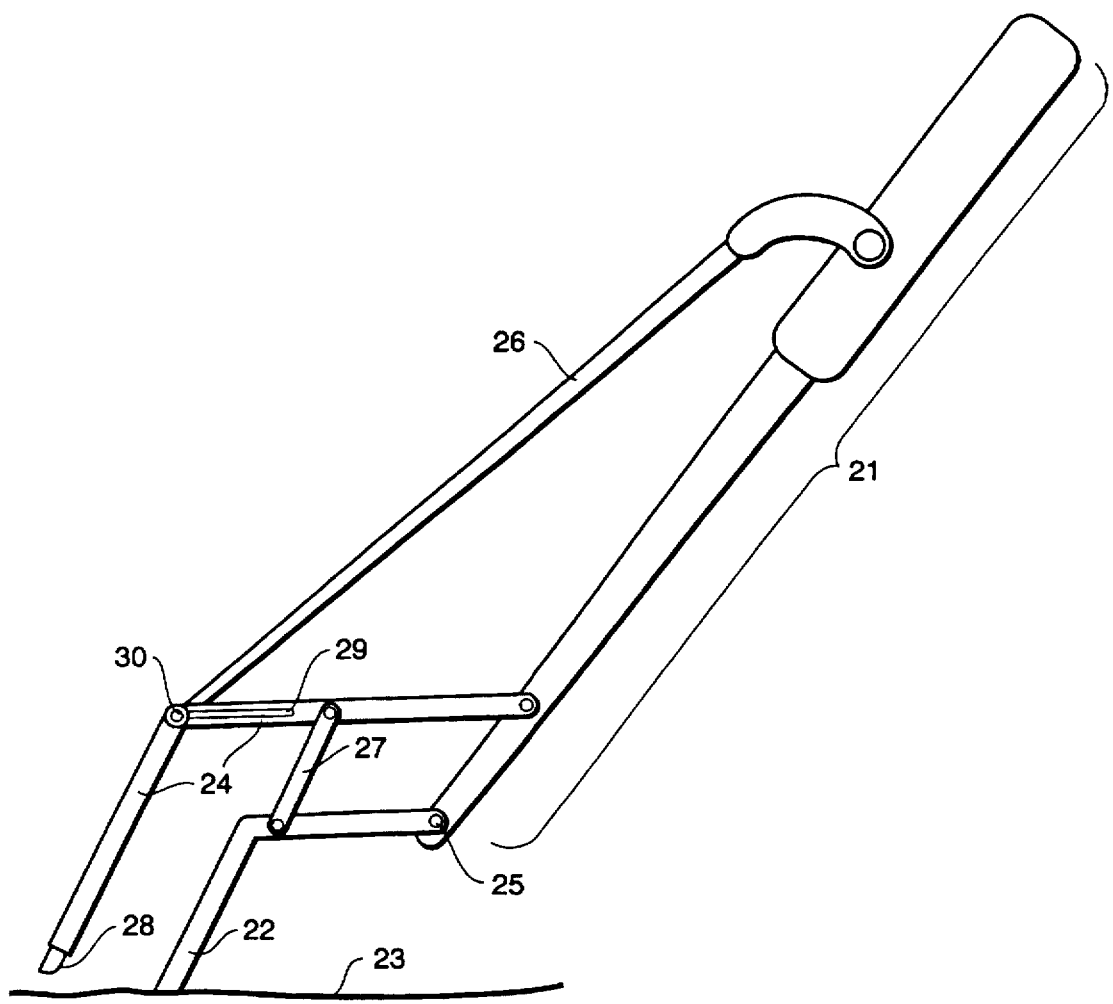
FIG. 7 is an embodiment of the invention featuring a motion-cancelling device incorporated into the cutting instrument.

Referring to FIG. 7, a further alternative embodiment of the invention, which is useful for making an incision in any moving structure, is comprising of a fixed handle 21 with blunt stylus point 22 that rests on the surface of a moving vessel 23 and moves freely in conjunction therewith. The instrument has a blade member 24 with a cutting edge 27 and freely moves relative to the moving vessel 23, and moves in conjunction with the blunt stylus point 22, but which may be controlled from a fixed handle 21. The motion of the blunt stylus point 22 helps to compensate for the movement of the moving vessel 23 relative to the visual field of the surgeon. In one embodiment, the fixed handle 21 is grasped by the surgeon, at the distal end thereof. The blunt stylus point 22 is affixed to the fixed handle 21 by a pivot joint 25 which may be lightly damped or spring tensioned such that the blunt stylus point 22 rests against the moving vessel 23 and maintains continuous contact therewith. The blade member 24 is preferably attached to the fixed handle 21, intermediate to the pivot joint 25 and a control lever 26 which is attached to the fixed handle 21 and to the blade member 24 so that the blade can be moved independent of the blunt stylus point 22 to contact the moving vessel 23 structure where the incision is to be made. The blade member 24 is attached to the blunt stylus point 22 with a rigid interconnecting shaft 27 so that the blade member 24 moves in tandem with the blunt stylus point 22 relative to any structure in contact with the blunt stylus point 22. The control lever 26 is slidably connected to the blade member 24 by providing a pin 30 at the end of the control lever 26 at the point of attachment to the blade member 24 and which is disposed to slide within a slot 29 in the blade member 24 thereby permitting the cutting edge 28 to operate below the level of the blunt stylus 22 to create the incision in the moving vessel 23.

The particular examples set forth herein are instructional and should not be interpreted as limitations on the applications to which those of ordinary skill are able to apply this invention. Modifications and other uses are available to those skilled in the art which are encompassed within the spirit of the invention as defined by the scope of the following claims.

What is claimed is:

1. A cutting instrument for making an incision having a predetermined length in the wall of a vessel, said cutting instrument comprising:

a shaft having proximal and distal ends, and having a handle on said proximal end;

a curved element integrally attached to said distal end, said curved element ending in a sharp pointed tip for penetrating a wall of a vessel, and including a concave blade on a proximal edge thereof, said concave blade extending between said pointed tip and said distal end of said shaft, said pointed tip being fixed a predetermined distance from said distal end of said shaft; and wherein said curved element is adapted to create a substantially linear incision in a wall of a vessel having a length corresponding substantially to said predetermined distance.

2. A cutting instrument for making an incision in the wall of a vessel comprising a blade, a shaft and a pointed end, wherein said blade is curved and is integrally attached to said shaft, said pointed end has a tip for penetrating a wall of a vessel, and said blade extends from said shaft to said pointed end, wherein said blade includes a substantially round surface opposite a concave cutting edge of said blade.

* * * * *